United States Patent
Parker et al.

(10) Patent No.: US 7,964,205 B2
(45) Date of Patent: Jun. 21, 2011

(54) INSECTICIDE AND MOLLUSCICIDE COMPOSITION AND METHODS

(75) Inventors: Diana L. Parker, Brentwood Bay (CA);
Cameron D. Wilson, Victoria (CA);
George S. Puritch, Saanichton (CA);
David S. Almond, Victoria (CA)

(73) Assignee: W. Neudorff GmbH KG, Emmerthal (DE)

( * ) Notice: Subject to any disclaimer, the term of this patent is extended or adjusted under 35 U.S.C. 154(b) by 1151 days.

(21) Appl. No.: 11/531,347

(22) Filed: Sep. 13, 2006

(65) Prior Publication Data

US 2007/0148203 A1    Jun. 28, 2007

Related U.S. Application Data

(60) Provisional application No. 60/718,246, filed on Sep. 16, 2005.

(51) Int. Cl.
*A01N 25/12* (2006.01)
*A01N 43/22* (2006.01)
*A01N 59/16* (2006.01)

(52) U.S. Cl. .......... 424/410; 424/84; 424/405; 424/406; 424/646; 424/647; 424/648; 514/28; 514/31; 514/140; 514/141; 514/142; 514/502; 514/557; 514/561; 514/574

(58) Field of Classification Search .......... None
See application file for complete search history.

(56) References Cited

U.S. PATENT DOCUMENTS

| | | | |
|---|---|---|---|
| 4,774,234 A | 9/1988 | Puritch et al. | |
| 4,826,678 A | 5/1989 | Gaudet et al. | |
| 5,093,124 A | 3/1992 | Kulenkampff et al. | |
| 5,362,634 A | 11/1994 | Boeck et al. | |
| 5,437,870 A | 8/1995 | Puritch et al. | |
| 5,631,290 A | 5/1997 | Almond et al. | |
| 5,700,473 A | 12/1997 | Puritch et al. | |
| 6,093,416 A | 7/2000 | Young et al. | |
| 6,352,706 B1 | 3/2002 | Puritch et al. | |
| 6,455,504 B1 | 9/2002 | Lewer et al. | |
| 6,703,036 B1 | 3/2004 | Young et al. | |
| 6,727,228 B2 | 4/2004 | Janssen et al. | |
| 7,530,196 B2 * | 5/2009 | Tidow et al. | 47/48.5 |
| 7,537,778 B2 * | 5/2009 | Parker | 424/410 |

FOREIGN PATENT DOCUMENTS

| | | | |
|---|---|---|---|
| EP | 1082014 A1 | 3/2001 | |
| EP | 001312260 A1 * | 5/2003 | |
| WO | WO-9933343 A2 | 7/1999 | |
| WO | 9960857 A1 | 12/1999 | |
| WO | 0170028 A1 | 9/2001 | |
| WO | 03024223 A1 | 3/2003 | |

OTHER PUBLICATIONS

Thompson, G.D., R. Dutton and T.C. Sparks. 2000. Spinosad—a case study: and example from a natural products discovery program. *Pest Management Science* 56: 696-702.
Cowles, R.S. et al. 2000. Inert formulation ingredients with activity: toxicity of trisiloxane surfactant solutions to twospotted mites. *J. Econ. Entomol.* 93(2): 180-188.
Tjosvold, S.A. and W.E. Chaney. 2001. Evaluation of reduced risk and other biorational miticides on the control of spider mites (*Tetranychus urticae*). *Acta Hort.* 547: 93-96.
Thompson, G.D. et al. 1999. Development of Spinosad and attributes of a new class of insect control products. University of Minnesota IPM Network.
Grossman, J. 1990. Horticultural oils: new summer uses on ornamental plant pests. The IPM Practitioner. vol. XII, No. 8, p. 1.
Canadian Office Action for corresponding Canadian Patent Application Serial No. 2,626,007, dated Jan. 29, 2010, (3 pages).
International Search Report WO2007/031565 A3, dated Apr. 18, 2007.
International Search Report WO2007/031561 A3, dated Apr. 17, 2007.
Thompson, G. D., K. H. Michel, R. C. Yao, J. S. Mynderse, C. T. Mosbert, T. V. Worden, E. H. Chio, T. C. Sparks and S. H. Hutchins. 1997. The discovery of *Saccharopolyspora spinosa* and a new class of insect control products. Down to Earth 52:1-5.
Cowles, R. S. 1998. Effect of spinosad formulations and other miticides on two spotted spider mite. 1995. Arthropod Manag. Tests 23:342-343.
R. Weinzerl. 2006. Alternatives to pyrethroids for managing corn earworm in sweet corn, seed corn, tomatoes and peppers. Pest Management Network. Jul. 2007.

* cited by examiner

*Primary Examiner* — Neil Levy
(74) *Attorney, Agent, or Firm* — Nutter McClennen & Fish LLP

(57) ABSTRACT

Bait compositions of spinosyns in combination with metal complexones and other mollusicides are provided in an environmentally safe composition that is effective to a treat and/or control a wide spectrum of insect and mollusc pests.

14 Claims, No Drawings

INSECTICIDE AND MOLLUSCICIDE COMPOSITION AND METHODS

CROSS-REFERENCE TO RELATED APPLICATIONS

This application claims priority to U.S. Provisional Application No. 60/718,246, filed on Sep. 16, 2005, and entitled "Wide Spectrum Insecticide and Molluscicide Composition," the disclosure of which is incorporated by reference herein.

FIELD OF THE INVENTION

The present invention relates to compositions and methods for treatment of insects and molluscs on plants and plant products, and in particular to compositions and methods that protect plants and plant products from damage caused by a wide spectrum of insect and mollusc pests.

BACKGROUND

Insect and mollusc pests cause significant losses to plants and plant products, and it is a major goal for those involved in plant care to control insect and mollusc pests in ways that protect the environment while, at the same time, are effective in combating both insect and mollusc pests. Several environmentally friendly active compounds have been identified and developed for use in the home and garden markets as well as in commercial agriculture. However many of these substances have a narrow range of pest control, thus requiring the application of multiple compositions to provide adequate pest control.

Accordingly, there remains a need for an improved composition to treat and prevent plant and plant product damage caused by insect and mollusc pests.

SUMMARY

The present invention provides various compositions and methods for the treatment of insects and molluscs on plants and plant products, and in particular to compositions and methods that protect plants and plant products from damage caused by a wide spectrum of insect and mollusc pests. In one aspect, an environmentally safe, non-phytotoxic insecticidal/molluscicidal bait composition is provided that includes an active amount of at least one spinosyn, at least one molluscicide, and at least one bait carrier. In use, the composition is effective to kill insects and molluscs without damaging plants or plant products.

The molluscicide can be selected from a variety of compounds, such as an iron salt, a metal compound and a chelator, a transition metal complexone, and synthetic molluscicides. In one embodiment, exemplary iron salts can include iron phosphate.

In another embodiment, the molluscicide can include a metal compound and a chelator. For example, such a compound can include a combination of a first component such as metal proteins, metal salts, metal carbohydrates, or combinations thereof combined with a second component that may be an aminopolycarboxylic acid chelator, a polyphosphonate chelator, and combinations thereof. Exemplary metals can include iron, copper, zinc, and aluminum. Exemplary aminopolycarboxylic acid chelators can include edetic acid, calcium disodium edetate, monosodium edetate, disodium edetate, trisodium edetate, tetrasodium edetate, calcium disodium hydroxyethylethylenediaminetriacetate, monosodium hydroxyethylethylenediaminetriacetate, trisodium hydroxyethylethylenediaminetriacetate, diethylenetriamine pentaacetic acid, iminodisuccinic acid, iminodifumaric acid, iminoditartaric acid, iminodimaleic acid, ethylenediaminedifumaric acid, ethylenediaminedimalic acid, iminodimalic acid, ethylenediamineditartaric acid, ethylenediaminedimaleic acid, ethylene diamine disuccinic acid, isomers of ethylene diamine disuccinic acid, and exemplary polyphosphonate chelators can include aminotri(methylenephosphonic acid) (ATMP), hydroxyethyldiphosphonic acid (HEDP).

In another embodiment, the molluscicide can be a transition metal complexone. Exemplary transition metal complexones can include a transition metal compound having metals such as iron, copper, zinc, aluminum, and mixtures thereof complexed with a chelator such as aminopolycarboxylic chelators, polyphosphonate chelators, and combinations thereof. Exemplary transition metal complexones can include ferric ethylene diamine tetracetate, ferrous ethylene diamine tetracetate, ferric hydroxyethylethylene diamine triacetate, ferrous hydroxyethylethylene diamine triacetate, ferric ethylene diamine disuccinate, ferrous ethylene diamine disuccinate, copper ethylene diamine disuccinate, zinc ethylene diamine disuccinate, aluminum ethylene diamine disuccinate, and mixtures thereof and their species and salts.

Additionally and/or alternatively, the molluscicide can be a synthetic molluscicide such as metaldehyde, methiocarb, carbaryl, isolan, mexcarbate, mercaptodimethur, niclosamide, trifenmorph, carbofuran, anarcardic acid, plant-derived saponins, lignosulfonates, lignosulfonate salts, boric acid, borate salts, and combinations thereof.

A variety of bait carriers can also be used to form the composition of the present invention, such as an insect/mollusc food. Exemplary insect/mollusc foods can include agar, potato dextrose agar, sugar beet, gelatin, oil cake, pet food, wheat, wheat flour, soya, oats, corn, rice, fruits, fish by-products, sugars, coated vegetable seeds, coated cereal seeds, casein, whey, blood meal, bone meal, yeast, paper products, natural clays, synthetic clays, talc, magnesium aluminum silicates, kaolinites, calcium carbonate, chalk, fats, cereals, and combinations thereof.

The composition can include a variety of other components depending upon the intended use. By way of non-limiting example, the composition can include a pH-adjusting agent that is selected from the group consisting of calcium carbonate, potassium carbonate, potassium hydroxide, ascorbic acid, tartaric acid, and citric acid. In use, the pH-adjusting agent results in the composition having a pH in the range of about 5 to 9 when measured as a dough prior to drying.

In another aspect, a method of exterminating unwanted molluscs and insect pests is provided that includes providing a composition having an effective amount of at least one spinosyn, at least one molluscicide, and at least one bait carrier, and administering an effective amount of the composition to an area infested with at least one of a mollusc and insect. The method can also include allowing at least one of a mollusc and insect to ingest the composition.

In another aspect, a method of preparing an insecticidal and molluscicidal bait is provided that includes blending at least one of a molluscicide, a spinosyn, and a carrier together to form a blended composition, adding a solvent to the composition to bind the bait, and forming the bait into at least one pellet.

In another aspect, a method of preparing an insecticidal and molluscicidal bait is provided that includes forming a core using at least one carrier, dispersing an amount of at least one of a spinosyn and a molluscicide in an oil to form a coating, and applying the coating to the core, such that at least one of the molluscicide and the spinosyn are bound to a surface of the core. In one embodiment, the method can further include forming a core from the carrier and at least one molluscicide, and dispersing an amount of a spinosyn in an oil to form a coating to coat a surface of the carrier and molluscicide core. In another embodiment, the method can further include forming a core from the carrier and at least one spinosyn, and dispersing an amount of a molluscicide in an oil to form a coating to coat a surface of the carrier and spinosyn core.

In yet another aspect, a method of preparing an insecticidal and molluscicidal bait is provided that includes blending at least one of a molluscicide, a spinosyn, and a carrier together to form a blended composition, adding a wax to the blended composition, and passing the blended composition through a pelletizing mechanism to effect binding of the wax to the composition, thereby forming at least one pellet.

DETAILED DESCRIPTION OF THE EXEMPLARY EMBODIMENTS

Certain exemplary embodiments will now be described to provide an overall understanding of the principles of the structure, function, manufacture, and use of the compositions and methods disclosed herein. One or more examples of these embodiments are illustrated in the accompanying tables. Those skilled in the art will understand that the compositions and methods specifically described herein are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides an environmentally safe and pesticidally effective composition to treat and prevent damage caused by insect and mollusc pests. In an exemplary embodiment, the composition can include spinosyns with at least one molluscicidally active composition. The compositions can be utilized as Ready-To-Use (RTU) baits, RTU liquid sprays, dusts, or liquid concentrates, depending upon the needs of the user. Exemplary bait formations can include any solid composition that can be spread on or around areas infested by insects and molluscs as well as in areas to prevent infestation of insects and molluscs, such as powders, granules, cubes, or pellets.

One skilled the art will appreciate that the compositions and methods disclosed herein can be used to treat a variety of home and garden insect and mollusc pests such as, by way of non-limiting example, members of the insect order Lepidoptera including Southern armyworm, codling moth, cutworms, clothes moths, Indian meal moth, leaf rollers, corn earworm, cotton bollworm (also called Tomato fruit worm), European corn borer, imported cabbageworm, cabbage looper, pink bollworm, American bolloworm, tomato hornworm, bagworms, Eastern tent caterpillar, sod webworm, diamondback moth, tomato pinworm, grape berry moth, cotton leafworm, beet armyworm, and fall armyworm; members of the order Homoptera including cotton aphid leafhoppers, plant hoppers, pear psylla, apple sucker, scale insects, whiteflies, and spittle bugs; and members of the insect order Diptera including house flies, stable flies, blow flies and mosquitoes, mites, and ants. The composition can also be used to treat members of the order Thysanoptera including melon thrips and Western flower thrips; members of the order Coleoptera, including Colorado potato beetles; members of the order Orthoptera; and Leaf miners of the orders Lepidoptera (moths and butterflies), Hymenoptera (leaf mining sawflies), Coleoptera (beetles), and Diptera (true flies). The composition is also effective against a wide variety of Molluscs including molluscs from the Family Arionidae, such as Arion ater, A. ruus, A. hortensis, and A. subfuscus; molluscs from the Family Limacide, such as Deroceras reticulatum; and molluscs from the Family Helicidae, such as Helix aperta and Helix aspersa. In exemplary embodiments, shown in Examples 1-11 below, the composition can be used to control and/or treat ants, earwigs, arion ater slugs, and deroceras reticulatum slugs.

As noted above, in one embodiment, the composition includes at least one spinosyn with at least one molluscicide and bait carrier in solid, dust, or liquid form. The spinosyns are macrolides that contain a tetracyclic ring system to which two different sugars are attached. In one embodiment, the spinosyn is isolated from the pesticidal fraction from the soil bacteria *Saccharopolyspora spinosa*, coded A83543. While the spinosyns can be isolated using a fermentation process, they are also commercially available under the brand names Conserve™ SC, SpinTor™, and Entrust™ (all from Dow AgroSciences LLC of 9330 Zionsville Road Indianapolis, Ind. 46268), Fire Ant Nightmare™ from Monterey Lawn and Garden Products, Inc. of P.O. Box 35000 Fresno, Calif., 93745-5000, and Bulls-Eye™ Bioinsecticide from Gardens-Alive! of 5100 Schenley Place, Lawrenceburg, Ind. 47025.

While an exemplary composition includes at least one spinosyn, the composition can also include other spinosyns. For example, the spinosyn can be spinosad, which is a mixture of two of the most active naturally occurring metabolites (spinosyns A and D). Spinosad, as used with the present invention, can be obtained from the commercially available product Entrusts™ from Dow, as noted above. Spinosad is a secondary metabolite from the aerobic fermentation of *S. spinosa* on nutrient media. Following fermentation, spinosad can be extracted and processed to form a highly concentrated conventional aqueous suspension for ease of use and distribution. Spinosad is a light gray to white crystalline solid with an earthy odor similar to slightly stale water. It has a pH of about 7.74, is stable to metal and metal ions for about 28 days, and has a shelf life of about three years as formulated material. It is also considered nonvolatile, and has vapor pressures around $10^{10}$ mm Hg. Spinosad is particularly advantageous in that it acts as both a contact and ingested toxin and it excites the insect nervous system, leading to involuntary muscle contractions, prostration with tremors, and paralysis. Spinosad also has effects on GABA receptor functions that may further contribute to its insecticidal activity.

Regardless of the form in which the composition is presented, e.g., liquid, RTU liquid spray, dust, or solid, the composition should include an amount of spinosyn that is effective to treat the particular insect or mollusc. In an exemplary embodiment, the concentration of spinosyn in the Ready-to-Use solid composition can be in the range of about 1 ppm to 20,000 ppm, more preferably about 1 ppm to 10,000 ppm, even more preferably about 10 ppm to 4,000 ppm, and most preferably about 100 ppm to 1,000 ppm. Moreover, the pH of the applied composition can be adjusted to be acidic, alkaline, or neutral, depending upon the particular needs of the user. An exemplary pH is in the range of about 6 to 7.

In one exemplary embodiment, spinosyns can be combined with at least one molluscicide and at least one bait carrier to form an environmentally safe, non-phytotoxic insecticidal and molluscicidal composition. A variety of molluscicides can be used to form the compositions disclosed herein, however the molluscicide preferably is an ingestible poison that is lethal to terrestrial molluscs. The molluscicide can be selected from a variety of compounds, such as an iron salt, a metal compound and a chelator, a transition metal complexone, and synthetic molluscicides. In one embodiment, exemplary iron salts can include iron phosphate.

In another embodiment, the molluscicide can include a metal compound and a chelator. Such a compound can be a combination of a first component (the metal compound) such as metal proteins, metal salts, metal carbohydrates, or combinations thereof combined with a second component that may be an aminopolycarboxylic acid chelator, a polyphosphonate chelator, and combinations thereof. Exemplary metals can include iron, copper, zinc, and aluminum. Exemplary aminopolycarboxylic acid chelators can include edetic acid, calcium disodium edetate, monosodium edetate, disodium edetate, trisodium edetate, tetrasodium edetate, calcium disodium hydroxyethylethylenediaminetriacetate, monosodium hydroxyethylethylenediaminetriacetate, trisodium hydroxyethylethylenediaminetriacetate, diethylenetriamine pentaacetic acid, iminodisuccinic acid, iminodifumaric acid, iminoditartaric acid, iminodimaleic acid, ethylenediaminedifumaric acid, ethylenediaminedimalic acid, iminodimalic acid, ethylenediamineditartaric acid, ethylenediaminedimaleic acid, ethylene diamine disuccinic acid, isomers of ethylene diamine disuccinic acid, imino disuccinic acid (IDS) or species or salts of these acids, and exemplary polyphosphonate chelators can include (methylenephosphonic acid) (ATMP), hydroxyethyldiphosphonic acid (HEDP), and combinations thereof.

In another embodiment, the molluscicide can be a transition metal complexone. Exemplary transition metal complexones can include a transition metal compound having metals such as iron, copper, zinc, aluminum, and mixtures thereof complexed with a chelator such as aminopolycarboxylic chelators, polyphosphonate chelators, and combinations thereof. Exemplary transition metal complexones can include ferric ethylene diamine tetracetate, ferrous ethylene diamine tetracetate, ferric hydroxyethylethylene diamine triacetate, ferrous hydroxyethylethylene diamine triacetate, ferric ethylene diamine disuccinate, ferrous ethylene diamine disuccinate, copper ethylene diamine disuccinate, zinc ethylene diamine disuccinate, aluminum ethylene diamine disuccinate, and mixtures thereof and their species and salts. Exemplary aminopolycarboxylic acid chelators and polyphosphonate chelators are noted above.

These compounds are particularly advantageous in that they are formed of constituent compounds which do not pose any significant threat to the environment, plants, animals, and other non-pests. The molluscicides can also be used in a variety of amounts, depending upon the needs of the user, however in one embodiment, when the composition is a solid, the molluscicides are present at a concentration in the range of about 0.1% to 10%, more preferably in the range of about 0.2% to 8%, and most preferably in the range of about 0.5% to 6%.

In another embodiment, the molluscicide can be a synthetic molluscicide such as metaldehyde, methiocarb, carbaryl, isolan, mexcarbate, mercaptodimethur, niclosamide, trifenmorph, carbofuran, anarcardic acid, plant-derived saponins, lignosulfonates, lignosulfonate salts, boric acid, borate salts, and mixtures thereof. Alternatively, the synthetic molluscicide can be present as a second molluscicide in the composition. Metaldehyde, which is a polymerization product of acetaldehyde, is sold in a variety of formulations, including brands such as Deadline 40 Deadline bullets produced by Monterey AgResources of P.O. Box 35000 Fresno, Calif. 93745-5000. The formulation of metaldehyde can include about 2 percent to 6 percent by weight active ingredient. Methiocarb is a carbamate, 4-methylthio-3,5-xylyl methyl-carbamate, sold under various brands including Mesurol 2% for homeowner use (produced by Gowan Co of P.O. Box 5569 Yuma, Ariz. 85366). While Methiocarb can be available in a variety of concentrations, in an exemplary embodiment, it has about 2% active ingredient.

In one embodiment, the composition can include a spinosyn(s) plus a single molluscicidal active ingredient in combination with an edible inert bait carrier. The single active ingredient can be an iron salt, or a metal chelate such as iron ethylenediamine disuccinate, ferric iron edetate, iron iminodisuccinate, iron hydroxyethylene diaminetriacetate, iron aminotri(methylenephosphonate), iron hydroxyethyldiphosphonate, and combinations thereof. Preferably, the active ingredient is present in an amount such that the concentration of iron within the composition is in the range of about 200 ppm to 60,000 ppm. Metal complexones, such as those which are discussed in U.S. Pat. Nos. 5,437,870; 6,352,706; 6,093,416; 6,703,036; and 6,852,329, which are herein incorporated by reference, can also be used. The iron salts are also sold in the market under various brand names such as Sluggo™ (available from Monterey Lawn and Garden Products, Inc.), and have iron phosphate as the active ingredient. In alternate embodiments, the composition can include two or more molluscicides, and the two or more molluscicides can include any of the molluscicides disclosed herein.

The above listed molluscicides are particularly advantageous in that they are not active against insect pests and thus, they are ideal for combining with various formulations of spinosyns to obtain a wide spectrum insect plus mollusc pesticide.

As noted above, the composition can also include a bait that is adapted to draw the pests to the composition such that it can be readily consumed by insects and molluscs. A variety of baits are well known and can be used in the compositions of the present invention. Exemplary baits can include an insect/mollusc food such as agar, potato dextrose agar, sugar beet, gelatin, oil cake, pet food, wheat, wheat flour, soya, oats, corn, rice, fruits, fish by-products, sugars, coated vegetable and cereal seeds, casein, whey, blood meal, bone meal, yeast, paper products, natural and synthetic clays such as diatomaceous earth, talc, magnesium aluminum silicates, kaolinites, calcium carbonate, chalk, fats including suet and lard, a variety of cereals including wheat cereal, and combinations thereof. In an exemplary embodiment, the bait is a wheat cereal, which is commercially available from, for example, Cargill, Inc. of P.O. Box 9300 Minneapolis, Minn. In other embodiments, where the composition is a dust or a liquid, the composition can include a dry carrier and/or a solvent, respectively.

One skilled in the art will appreciate that the spinosyn-containing compositions disclosed herein are not only pesticidally effective, but also environmentally sound and safe for human use. Further, some of the compositions can be residual in that they do not leach out of baits during rain, and thus can protect against insect and mollusc pests during and after rainy weather. One skilled in the art will appreciate that a variety of other compounds can be added to the insecticidal/molluscicidal composition depending upon the needs of the user. In one embodiment surfactants, and preferably non-ionic and amphoteric surfactants, can be useful in the composition. Preferred nonionic surfactants include ethoxylated sorbitan derivatives, ethoxylated fatty acids, and mixtures thereof. Exemplary ethoxylated sorbitan derivatives include TWEEN surfactants, such as TWEEN 81 and TWEEN 85, available from ICI Americas, Inc., Agricultural Products Division of Wilmington, Del. Other suitable sorbitan derivatives include EMSORB 6903 and EMSORB 6913, available from Henkel Corp. of Cincinnati, Ohio. Suitable ethoxylated fatty acids include CHEMAX T09 and CHEMAX E400MO available from Chemax, Inc. of Greenville, S.C., and ALKASURF 014 and ALKASURF 09, available from Rhone Poulenc of Cranberry, N.J. Preferred amphoteric surfactants include cetyl (C16) betaine, known chemically as 1-hexadecanaminium, N-(carboxymethyl)N,N-dimethyl-, inner salt (CAS number 693-334) available, from Deforest Enterprises Fla., USA.

In another embodiment, antioxidants can be added to the composition in order to reduce the effect of oxidation of the composition. Examples of suitable antioxidants include butylated hydroxytoluene (BHT), butylated hydroxy anisole (BHA), alpha-tochopherol, ethoxyquin (6-ethoxy-2,2,4-trimethyl-1,2-dihydroquinoline), and 2,6-dioctadecyl-P-cresol (DOPC).

The composition can also include a pH-adjusting agent. While a variety of pH-adjusting agents can be used, exemplary pH-adjusting agents can include calcium carbonate, potassium carbonate, potassium hydroxide, ascorbic acid, tartaric acid, and citric acid. In use, the pH-adjusting agent results in the composition having a pH in the range of about 5 to 9 when measured in the carrier prior to drying.

One skilled in the art will appreciate that the insecticidal/molluscicidal composition can also include additional formulation enhancing additives, such as preservatives or anti-microbial agents, phagostimulants, ultra violet protectants, antioxidants, waterproofing agents, taste altering additives, or any combination thereof.

A variety of preservatives can be used effectively with the insecticidal/molluscicidal composition of the present invention, and exemplary preservatives include Legend MK® available from Rohm & Haas Company of Philadelphia, Pa., and CA-24 available from Dr. Lehmann and Co. of Memmingen/Allgäu, Germany. While the preservatives can be present in the composition in a variety of amounts, preferably the preservatives, such as those listed above for example, can be mixed with water to form a stock solution to be added to the formulation at a concentration in the range of about 1 ppm to 750 ppm.

Phagostimulants can be added to the composition to attract insects and molluscs and to induce them to feed upon the composition. A variety of phagostimulants can be used, including sugars, yeast products, and casein, and in an exemplary embodiment sugars, such as sucrose, are used. These additives are normally incorporated within the composition in a dry form in a variety of amounts, however typically, they can be added to the composition at about 1 percent by weight to 2.5 percent by weight of the total composition.

Waterproofing agents, which can also act as binders, can also be added to the composition to improve the composition's weatherability. These are typically water insoluble compounds such as waxy materials and other hydrocarbons. Examples of suitable waterproofing agents are paraffin wax, stearate salts, beeswax, and similar compounds. One preferred wax compound is PAROWAX®, available from Conros Corp. of Scarborough, Ontario, Canada. Waterproofing agents can be incorporated into the composition in dry form in a variety of amounts, however in an exemplary embodiment waterproofing agents are incorporated into the composition at about 5 percent by weight to 12 percent by weight of the total composition.

The composition can also include an insecticidal/molluscicidal taste altering compound to render the composition unpalatable to animals. Exemplary compositions include those having a bitter taste, and suitable compounds that are commercially available include BITREX, available from McFarlane Smith Ltd. of Edinburgh, Scotland. These compounds typically are added at very low concentrations, and, for example, a 0.1% BITREX solution can typically be added to the composition at about 1 percent by weight to 2 percent by weight of the total composition.

The insecticidal/molluscicidal composition of the present invention typically is used in dry form and many of the constituent ingredients of the composition are included in dry form. However, it can be useful to include a sufficient amount of water within the composition to form the bait so that the ingredients can be more easily formed. While the amount of water added can vary, water is typically added at about 15 percent by weight to 60 percent by weight of the total composition. This water, however, typically is driven off by heating and drying the composition before the composition is used.

Dry insecticidal/molluscicidal compositions according to the present invention can be prepared using a variety of techniques. In one embodiment, a suitable amount of the spinosyn and molluscicide, such as Spinosad and iron EDTA for example, can be blended in dry form with dry bait, such as wheat flour. Thereafter, other dry ingredients (such as phagostimulants and waterproofing agents, for example) can be blended and mixed with the composition. Suitable amounts of liquid additives (such as preservatives, taste altering additives and solvents such as water, for example) can also be added to the dry mixture to form a dough. The composition is then preferably covered, such as with plastic wrap, and heated. While a variety of techniques can be used to heat the composition, in one embodiment, the composition can be heated in a microwave oven for a time in the range of about 30 seconds to 10 minutes, depending upon the make-up of the composition. After heating, the dough can be processed in a food grinder to obtain strands of the composition, which can be dried, at elevated or ambient temperatures, and made into a desired form, such as powder, pellets, cubes, or granules, for example. In other embodiments, the spinosyn, the molluscicide, and a bait carrier can be blended together to form a blended composition. A binding agent, such as wax, can then be added to the composition, and the composition can be passed through a pelletizing mechanism to activate the binding agents. While the pelletizing agent can vary depending upon the type of binding agent used, when the binding agent is wax, the wax can be heated such that it is melted.

In yet another embodiment, the bait can be formed using a technique that first forms a bait pellet from a bait carrier, and then adds a molluscicide and a spinosyn as a coating around the pellet. For example, where the bait pellet is formed from a bait carrier, a molluscicide and a spinosyn can be dispersed in an oil (such as mineral oil, triglyceride oil, and combinations thereof) to form a coating solution. This coating solution can then be applied to the bait carrier pellet, such that it coats the pellet. Alternatively, in other embodiments, either the molluscicide or the at least one spinosyn can be incorporated within the carrier core and the other of the molluscicide and the spinosyn can be dispersed in an oil and used to coat the resulting pellet. For example, in one embodiment, the method can forming a core from the carrier and at least one molluscicide, and dispersing an amount of a spinosyn in an oil to form a coating to coat a surface of the carrier and molluscicide core. In another embodiment, the method can include forming a core from the carrier and at least one spinosyn, and dispersing an amount of a molluscicide in an oil to form a coating to coat a surface of the carrier and spinosyn core. One skilled in the art will appreciate the variety of techniques that can be used to form a bait pellet.

An exemplary formulation of a composition effective for treating insect and mollusc pests can be as follows:

|  | Ingredient | Quantity |
|---|---|---|
| Dry Components | Wheat flour | 95.4 g |
|  | Spinosad | 0.1 g |
|  | Active Ingredient Molluscicide | 2.0 g |
|  | Sucrose | 2.50 g |
| Liquid | Water | 30.00 g |
|  | TOTAL | 130.00 g |

The following non-limiting examples serve to further describe the invention. In all of the examples, the percent of the active ingredient is on a weight percent basis.

EXAMPLE 1

Test of Spinosad and Fatty Acid Salt Combination to Control Earwigs

The purpose of this test was to evaluate Spinosad for controlling *F. auricularia* (European earwigs). Following the formation of a dry insecticidal/molluscicidal bait using the commercially available form of spinosyn Spinosad and Sluggo™ (which contains iron phosphate as the active ingredient), earwigs were placed into tubs containing sand that was moistened with water. The sand was covered by a layer of wet paper toweling and the bait noted in Table 1 were placed on top of the paper. Each treatment consisted of 2 replicates of 10 earwigs each and 1 g of bait. The boxes were placed inside a cardboard box and left in a shaded place in the laboratory, and mortality was assessed at 5, 7, and 12 days following treatment.

Table 1, below, illustrates the results obtained from compositions of Spinosad, fatty acid salts, and combinations thereof.

TABLE 1

Effect of compositions of Spinosad and fatty acid salts on earwigs.

| Compound | Number of Dead Earwigs (compared to total number of earwigs) | Mean % Mortality after 12 days |
|---|---|---|
| Sluggo ™ plus 0.015% ai Spinosad | 11/21 | 52.4 |
| Sluggo ™ plus 0.03% ai Spinosad | 15/20 | 75.0 |
| Sluggo ™ plus 0.1% ai Spinosad | 19/20 | 95.0 |
| Sluggo ™ plus 0.32% ai Spinosad | 17/20 | 85.0 |
| Sluggo ™ | 1/20 | 5.0 |
| Control | 2/20 | 10.0 |

EXAMPLE 2

Test of Spinosad and Cannola Oil Combination to Control Ants

The purpose of this test was to evaluate Spinosad in combination with cannola oil for controlling ants. Following the formation of Spinosad-based dry insecticidal/molluscicidal baits, ants were each placed into petri dishes. 1.0 g of the baits noted below in Table 2 were placed into each dish, and the petri dishes were secured to prevent escapes. Each treatment consisted of 8 replicates of 5 insects, and mortality was assessed at 1, 2, and 5 days following treatment.

TABLE 2

Effect of compositions of Spinosad and cannola oil on ants.

| Compound | Mean % Mortality (after 2 days) | Mean % Mortality (after 5 days) |
|---|---|---|
| Sluggo ™ plus 0.015% ai Spinosad | 12.5 | 70.0 |
| Sluggo ™ plus 0.015% ai Spinosad plus 1% canola oil | 2.5 | 35.0 |
| Sluggo ™ plus 0.015% ai Spinosad + 5% canola oil | 27.5 | 77.5 |
| Sluggo ™ plus 0.015% ai Spinosad (Spinosad dispersed in 1% canola oil) | 27.5 | 82.5 |
| Sluggo ™ plus 0.015% ai Spinosad (Spinosad dispersed in 5% canola oil) | 32.5 | 77.5 |
| Sluggo ™ | 0.0 | 7.5 |
| Untreated | 0.0 | 0.0 |

EXAMPLE 3

Test of Spinosad and Iron Phosphate Bait Combination to Control Earwig Nymphs

The purpose of this test was to evaluate spinosad in combination with iron phosphate baits for controlling earwig nymphs. Following formation of compositions of dry insecticidal/molluscicidal bait using spinosad, earwig nymphs were placed tubs. The tubs contained a 1 cm depth of moist potting soil with a single radish plant (2-3 leaves) planted in the middle. Each treatment consisted of 1.0 g of the baits noted in Tables 3 and 4 sprinkled around the base of the plants. Each treatment consisted of 5 replicates of 10 earwig nymphs each, and mortality and was assessed at 1, 2, 3, 6, and 7 days following treatment.

TABLE 3

Effects of compositions of iron phosphate bait and spinosad on earwig nymphs.

| Compound | Mean % Mortality (after 1 day) | Mean % Mortality (after 2 days) | Mean % Mortality (after 3 days) | Mean % Mortality (after 7 days) |
|---|---|---|---|---|
| Iron phosphate bait plus 0.07% ai Spinosad ™ | 56.3 | 41.6 | 73.8 | 93.6 |
| Iron phosphate bait | 0.0 | 0.0 | 6.3 | 9.0 |
| Untreated | 0.0 | 4.8 | 12.2 | 12.4 |

TABLE 4

Consumption of radish plants by European earwig nymphs exposed to compositions of iron phosphate bait and spinosad.

| Compound | Mean % Consumption (after 3 days) | Mean % Consumption (after 6 days) |
|---|---|---|
| Iron phosphate bait plus 0.07% ai Spinosad | 10.4 | 30.0 |
| Iron phosphate bait | 29.0 | 48.0 |
| Untreated | 54.0 | 86.0 |

EXAMPLE 4

Test of Spinosad and Iron Bait Combination to Control Adult Earwigs

The purpose of this test was to evaluate spinosad in combination with iron bait for controlling adult earwigs. Following formation of compositions of dry insecticidal/molluscicidal bait using spinosad, earwig adults and 1.0 g of the bait compositions noted in Table 5 were placed in the dishes. Each treatment consisted of 8 replicates of 5 earwigs each, and mortality was assessed at 1, 2, 3, 6, 7, 8, 10, 13, and 14 days following treatment.

TABLE 5

Effects of compositions of iron baits and spinosad combinations on the mortality of adult earwigs.

| Compound | Mean % Mortality (after 1 day) | Mean % Mortality (after 3 days) | Mean % Mortality (after 6 days) | Mean % Mortality (after 7 days) | Mean % Mortality (after 13 days) |
|---|---|---|---|---|---|
| Iron phosphate bait plus 0.07% ai Spinosad | 10.0 | 32.5 | 47.5 | 60.0 | 80.0 |
| Iron EDTA bait plus 0.07% ai Spinosad | 0.0 | 10.0 | 27.5 | 40.0 | 52.5 |
| Untreated | 0.0 | 0.0 | 0.0 | 0.0 | 5.0 |

EXAMPLE 5

Test of Spinosad and Iron Bait Combination to Control Adult Earwigs

The purpose of this test was to evaluate spinosad in combination with iron bait for controlling adult earwigs. Following formation of compositions of dry insecticidal/molluscicidal bait using spinosad, earwig adults and 1.0 g of the bait compositions noted in Table 6 were placed in the dishes. Each treatment consisted of 8 replicates of 5 earwigs each, and mortality was assessed at 1, 2, 5, and 6 days following treatment.

TABLE 6

Effects of compositions of iron baits and spinosad combinations on the mortality of adult earwigs

| Compound | Mean % Mortality (after 1 day) | Mean % Mortality (after 2 days) | Mean % Mortality (after 5 days) | Mean % Mortality (after 6 days) |
|---|---|---|---|---|
| Iron phosphate bait plus 0.07% ai Spinosad | 60.0 | 72.5 | 92.5 | 95.0 |
| Iron EDTA bait plus 0.07% ai Spinosad | 50.0 | 75.0 | 85.0 | 87.5 |
| Untreated | 2.5 | 0.0 | 10.0 | 10.0 |

EXAMPLE 6

Test of Spinosad and Sluggo™ Combinations to Control Slugs

The purpose of this test was to evaluate spinosad in combination with Sluggo™ for controlling slugs. Following the formation of baits noted below in Tables 7 and 8, 10 *Arion ater* slugs were placed in tubs. Each tub received one young potted lettuce plant and 5 grams of bait, with two tubs per bait formulation. The tubs were kept outdoors for the test period, and mortality was observed at 5 and 7 days following treatment.

TABLE 7

Effects of compositions of spinosad and Sluggo ™ combinations on the mortality of slugs at 5 days after treatment.

| | Trial 1 | | Trial 2 | |
|---|---|---|---|---|
| Compound | Number of dead slugs (compared to total number of slugs) | % of plant eaten | Number of dead slugs (compared to total number of slugs)) | % of plant eaten |
| Sluggo ™ 0.015% ai Spinosad | 9/10 | 0 | 10/10 | 0 |
| Sluggo ™ 0.03% ai Spinosad | 9/10 | 0 | 9/10 | 0 |
| Sluggo ™ 0.07% ai Spinosad | 9/10 | 0 | 9/10 | 0 |
| Sluggo ™ 0.10% ai Spinosad | 10/10 | 0 | 10/10 | 0 |
| Sluggo ™ 0.32% ai Spinosad | 8/10 | 0 | 6/10 | 0 |
| Sluggo ™ | 9/10 | 0 | 9/10 | 0 |
| Control | 0/10 | 100 | 0/10 | 100 |

TABLE 8

Effects of compositions of spinosad and Sluggo ™ combinations on the mortality of slugs at 7 days after treatment.

| Compound | Number of dead slugs (compared to total number of slugs) | % of slugs killed |
|---|---|---|
| Sluggo ™ 0.015% ai Spinosad | 20/20 | 100 |
| Sluggo ™ 0.03% ai Spinosad | 18/20 | 90 |
| Sluggo ™ 0.07% ai Spinosad | 20/20 | 100 |
| Sluggo ™ 0.10% ai Spinosad | 20/20 | 100 |
| Sluggo ™ 0.32% ai Spinosad | 18/20 | 90 |
| Sluggo ™ | 18/20 | 90 |
| Control | 0/20 | 0 |

EXAMPLE 7

Test of Spinosad and Sluggo Combinations to Control Slugs

The purpose of this test was to evaluate spinosad in combination with Sluggo™ for controlling slugs. Following the formation of the baits noted below in Table 9, the baits along with 15 *Deroceras reticulatum* slugs were placed into tubs. Each tub received one young potted lettuce plant and 2 grams of bait, and there were two tubs per bait formulation. The tubs were kept in the shade outdoors for the test period, and morality was assessed after 7 days.

TABLE 9

Effects of compositions of spinosad and Sluggo ™ combinations on the mortality of slugs.

| Compound | Number of dead slugs (compared to total number of slugs) | % of slugs killed |
|---|---|---|
| Sluggo ™ 0.07% ai Spinosad | 15/29 | 51.7 |
| Sluggo ™ 0.1% ai Spinosad | 20/30 | 66.7 |

TABLE 9-continued

Effects of compositions of spinosad and Sluggo ™ combinations on the mortality of slugs.

| Compound | Number of dead slugs (compared to total number of slugs) | % of slugs killed |
|---|---|---|
| Sluggo ™ | 18/30 | 60 |
| Control | 0/30 | 0 |

EXAMPLE 8

Test of Spinosad and Bait Combinations to Control Slugs

The purpose of this test was to evaluate spinosad in combination with Metarex™ or Sluggo™ for controlling slugs. Following the formations of baits as noted in Tables 10 and 11 below, *Deroceras reticulatum* slugs were collected from the field and added to the tubs the same day. Each tub received one young potted lettuce plant and 2 grams of bait, and there were two tubs per treatment. The tubs were kept in the laboratory for the test period, and mortality was assessed after 5 days.

TABLE 10

Effects of compositions of spinosad and bait combinations on the mortality of slugs.

| | Trial 1 | | Trial 2 | |
|---|---|---|---|---|
| Compound | Number of dead slugs (compared to total number of slugs) | % of plant eaten | Number of dead slugs (compared to total number of slugs)) | % of plant eaten |
| Metarex ™ (4% ai metaldehyde) | 1/10 | 90 | 3/10 | 20 |
| Metarex ™ (4% ai metaldehyde) coated with 700 ppm Spinosad (Entrust ™) | 3/10 | 60 | 7/10 | 0 |
| Sluggo ™ (1.0% iron phosphate ai) | 9/10 | 0 | 9/10 | 0 |
| Sluggo ™ (1.0% iron phosphate ai) coated with 700 ppm Spinosad (Entrust ™) | 9/10 | 0 | 10/10 | 0 |
| Control (standard bait made with wheat flour) | 0/10 | 100 | 0/10 | 100 |
| Control (standard bait made with wheat flour) coated with 700 ppm Spinosad (Entrust ™) | 0/10 | 30 | 0/10 | 100 |

TABLE 11

Effects of compositions of spinosad and bait combinations on the mortality of slugs.

| Compound | Number of dead slugs (compared to total number of slugs) | % of slugs killed |
|---|---|---|
| Metarex ™ (4% ai metaldehyde) | 4/20 | 20 |
| Metarex ™ (4% ai metaldehyde) coated with 700 ppm Spinosad (Entrust ™) | 10/20 | 50 |
| Sluggo ™ (1.0% iron phosphate ai) | 18/20 | 90 |
| Sluggo ™ (1.0% iron phosphate ai) coated with 700 ppm Spinosad (Entrust ™) | 19/20 | 95 |
| Control (standard bait made with wheat flour) | 0/20 | 0 |
| Control (standard bait made with wheat flour) coated with 700 ppm Spinosad (Entrust ™) | 0/20 | 0 |

EXAMPLE 9

Test of Spinosad and Bait Combinations to Control Slugs

The purpose of this test was to evaluate spinosad in combination with iron EDTA baits for controlling slugs. Following the formations of baits as noted in Tables 12 and 13 below, *Deroceras reticulatum* slugs were collected from the field and added to the tubs the same day. Each tub had 10 *Deroceras reticulatum* slugs, one young potted lettuce plant and 2 grams of bait, and there were two tubs per treatment. The tubs were kept in the laboratory for the test period, and mortality was assessed after 5 days.

TABLE 12

Effects of compositions of spinosad and bait combinations on the mortality of slugs.

| | Trial 1 | | Trial 2 | |
|---|---|---|---|---|
| Compound | Number of dead slugs (compared to total number of slugs) | % of plant eaten | Number of dead slugs (compared to total number of slugs)) | % of plant eaten |
| Iron EDTA (wheat flour bait made with 2.07% iron EDTA) | 10/10 | 0 | 9/10 | 0 |
| Iron EDTA (wheat flour bait made with 2.07% iron EDTA) plus 700 ppm Spinosad (Entrust ™) | 7/10 | 0 | 10/10 | 0 |

TABLE 12-continued

Effects of compositions of spinosad and bait combinations on the mortality of slugs.

|  | Trial 1 | | Trial 2 | |
| --- | --- | --- | --- | --- |
| Compound | Number of dead slugs (compared to total number of slugs) | % of plant eaten | Number of dead slugs (compared to total number of slugs)) | % of plant eaten |
| Iron EDTA (wheat flour bait made with 2.07% iron EDTA) coated with 700 ppm Spinosad (Entrust ™) | 9/10 | N/A* | 10/10 | N/A* |
| Sluggo ™ (1.0% iron phosphate ai) | 9/10 | 0 | 10/10 | 0 |
| Control (standard bait made with wheat flour) | 0/10 | 100 | 0/10 | 100 |
| Control (standard bait made with wheat flour) made with 700 ppm Spinosad (Entrust ™) | 0/10 | 100 | 0/10 | 85 |

*Plant was damaged by a fungal pathogen and could not be used for assessment.

TABLE 13

Effects of compositions of spinosad and bait combinations on the mortality of slugs.

| Compound | Number of dead slugs (compared to total number of slugs) | % of slugs killed |
| --- | --- | --- |
| Iron EDTA (wheat flour bait made with 2.07% iron EDTA) | 19/20 | 95 |
| Iron EDTA (wheat flour bait made with 2.07% iron EDTA) plus 700 ppm Spinosad (Entrust ™) | 17/20 | 85 |
| Iron EDTA (wheat flour bait made with 2.07% iron EDTA) coated with 700 ppm Spinosad (Entrust ™) | 19/20 | 95 |
| Sluggo ™ (1.0% iron phosphate ai) | 19/20 | 95 |
| Control (standard bait made with wheat flour) | 0/20 | 0 |
| Control (standard bait made with wheat flour) made with 700 ppm Spinosad (Entrust ™) | 0/20 | 0 |

EXAMPLE 10

Test of Spinosad and Bait Combinations to Control Earwigs

The purpose of this test was to evaluate spinosad in combination with various baits for controlling earwigs. Dry insecticidal/molluscicidal baits were made as noted in Table 14 below. Earwigs from a colony were placed in petri dishes with 1.0 g of bait placed on 4.0 g of sand moistened with 0.8 g of water in a 16 dram vial. Each treatment consisted of 5 replicates of 3 insects each, and mortality was assessed at 1, 2, and 3 days following treatment.

TABLE 14

Effects of compositions of spinosad and bait combinations on the mortality of earwigs.

| Compound | Mean % Mortality (after 1 day) | Mean % Mortality (after 2 days) | Mean % Mortality (after 3 days) |
| --- | --- | --- | --- |
| Iron phosphate bait plus 0.07% ai Spinosad | 46.7 | 53.3 | 60.0 |

TABLE 14-continued

Effects of compositions of spinosad and bait combinations on the mortality of earwigs.

| Compound | Mean % Mortality (after 1 day) | Mean % Mortality (after 2 days) | Mean % Mortality (after 3 days) |
| --- | --- | --- | --- |
| Metarex ™ bait coated with 0.07% ai Spinosad | 66.7 | 86.7 | 93.3 |
| Control | 0 | 0 | 0 |

EXAMPLE 11

Test of Spinosad and Bait Combinations to Control Ants

The purpose of this test was to evaluate spinosad in combination with Metarex™ bait for controlling ants. The bait was coated with various amounts of spinosad as shown in Table 15 below. Following formation of the bait, ants from a colony were placed in petri dishes along with 1.0 g of the baits. Each treatment consisted of 5 replicates of 5 insects, and mortality was assessed at 1, 2, and 3 days following treatment.

TABLE 15

Effects of compositions of spinosad and bait combinations on the mortality of ants.

| Compound | Mean % Mortality (after 1 day) | Mean % Mortality (after 2 days) | Mean % Mortality (after 3 days) |
| --- | --- | --- | --- |
| Metarex ™ bait coated with 0.07% ai Spinosad* | 40.0 | 88.0 | 100.0 |
| Control | 0 | 0 | 0 |

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of exterminating unwanted molluscs and insect pests, comprising:
providing a composition having an effective amount of at least one spinosyn present at a concentration in the range of about 1 ppm to 20,000 ppm, and at least one molluscicide, wherein the molluscicide is an iron compound and at least one chelator, and the spinosyn and iron are present in the composition at a ratio of spinosyn to iron in the range of about 1:2 to 1:6,000; and
administering an effective amount of the composition to an area infested with at least one of a mollusc and insect.

2. The method of claim 1, further comprising allowing the at least one of a mollusc and insect to ingest the composition.

3. The method of claim 1, wherein the at least one chelator is selected from the group consisting of aminopolycarboxylic chelators, polyphosphonate chelators, and combinations thereof.

4. The method of claim 1, wherein the at least one chelator is selected from the group consisting of edetic acid, calcium disodium edetate, monosodium edetate, disodium edetate, trisodium edetate, tetrasodium edetate, calcium disodium hydroxyethylethylenediaminetriacetate, monosodium hydroxyethylethylenediaminetriacetate, trisodium hydroxyethylethylenediaminetriacetate, diethylenetriamine pentaacetic acid, iminodisuccinic acid, iminodifumaric acid, iminoditartaric acid, iminodimaleic acid, ethylenediaminedifumaric acid, ethylenediaminedimaleic acid, iminodimaleic acid, ethylenediamineditartaric acid, ethylene diamine disuccinic acid, isomers of ethylene diamine disuccinic acid, salts of ethylene diamine disuccinic acid, metal complexes of ethylene diamine disuccinic acid, mixtures of ethylene diamine disuccinic acid, and combinations thereof.

5. The method of claim 1 wherein the at least one chelator is selected from the group consisting of aminotri(methylenephosphonic acid) (ATMP), hydroxyethyldiphosphonic acid (HEDP), and combinations thereof.

6. The method of claim 1, further comprising a pH-adjusting agent.

7. The method of claim 6, wherein the pH-adjusting agent is selected from the group consisting of calcium carbonate, potassium carbonate, potassium hydroxide, ascorbic acid, tartaric acid, and citric acid.

8. The method of claim 6, wherein the pH-adjusting agent results in the composition having a pH in the range of about 5 to 9 when measured as a dough prior to drying.

9. The method of claim 1, wherein the at least one molluscicide is present at a concentration in the range of about 0.1 to 10%.

10. The method of claim 1, wherein the composition further comprises an insect/mollusc food bait carrier.

11. The method of claim 10, wherein the insect/mollusc food is selected from the group consisting of agar, potato dextrose agar, sugar beet, gelatin, oil cake, pet food, wheat, wheat flour, soya, oats, corn, rice, fruits, fish by-products, sugars, coated vegetable seeds, coated cereal seeds, casein, whey, blood meal, bone meal, yeast, paper products, natural clays, synthetic clays, talc, magnesium aluminum silicates, kaolinites, calcium carbonate, chalk, fats, cereals, and combinations thereof.

12. The method of claim 1, wherein the iron compound and at least one chelator is an iron complexone.

13. The method of claim 12, wherein the iron complexone includes iron complexed with a chelator selected from the group consisting of aminopolycarboxylic chelators, polyphosphonate chelators, and combinations thereof.

14. The method of claim 12, wherein the iron complexone is selected from the group consisting of ferric ethylene diamine tetracetate, ferrous ethylene diamine tetracetate, ferric hydroxyethylethylene diamine triacetate, ferrous hydroxyethylethylene diamine triacetate, ferric ethylene diamine disuccinate, ferrous ethylene diamine disuccinate, and mixtures thereof and their species and salts.

* * * * *